(12) United States Patent
Gütlin et al.

(10) Patent No.: US 7,641,693 B2
(45) Date of Patent: Jan. 5, 2010

(54) INTERVERTEBRAL IMPLANT

(75) Inventors: Michael Gütlin, Pratteln (CH); Manuel Schär, Muttenz (CH); Beat Lechmann, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 222 days.

(21) Appl. No.: 11/259,538

(22) Filed: Oct. 25, 2005

(65) Prior Publication Data

US 2006/0100710 A1    May 11, 2006

Related U.S. Application Data

(63) Continuation of application No. PCT/CH03/00273, filed on Apr. 28, 2003.

(51) Int. Cl.
*A61F 2/44* (2006.01)
(52) U.S. Cl. .................................................... 623/17.15
(58) Field of Classification Search ... 623/17.11–17.16; 254/93 H, 93 R, 98, 103, 133 R
See application file for complete search history.

(56) References Cited

U.S. PATENT DOCUMENTS

| | | | | |
|---|---|---|---|---|
| 1,238,863 A | * | 9/1917 | Willour | 254/103 |
| 1,486,723 A | * | 3/1924 | Bernson | 254/102 |
| 1,896,715 A | * | 2/1933 | Martinetti | 254/1 |
| 6,193,756 B1 | * | 2/2001 | Studer et al. | 623/17.15 |
| 6,258,125 B1 | * | 7/2001 | Paul et al. | 623/17.11 |
| 6,730,088 B2 | * | 5/2004 | Yeh | 606/61 |
| 6,896,517 B1 | * | 5/2005 | Bjorn et al. | 433/174 |
| 7,022,138 B2 | * | 4/2006 | Mashburn | 623/17.13 |
| 2002/0082695 A1 | * | 6/2002 | Neumann | 623/17.11 |
| 2002/0161441 A1 | | 10/2002 | Lang et al. | |
| 2004/0186569 A1 | * | 9/2004 | Berry | 623/17.11 |
| 2006/0241770 A1 | * | 10/2006 | Rhoda et al. | 623/17.15 |
| 2007/0028710 A1 | * | 2/2007 | Kraus et al. | 74/400 |

FOREIGN PATENT DOCUMENTS

| | | |
|---|---|---|
| DE | 195 09 317 | 9/1996 |
| DE | 196 22 827 | 12/1997 |
| EP | 1 080 703 | 3/2001 |
| EP | 1 219 266 | 7/2002 |
| WO | WO 2004100837 A1 * | 11/2004 |

* cited by examiner

*Primary Examiner*—Thomas C Barrett
*Assistant Examiner*—Nicholas Woodall
(74) *Attorney, Agent, or Firm*—Stroock & Stroock & Lavan LLP

(57) ABSTRACT

An intervertebral implant having a lower implant part and an upper implant part. The lower implant part has an outer casing, a hollow cylindrical cavity, an axis of rotation, and an apposition part for contacting the lower vertebra. The upper implant part has an essentially circularly cylindrical shaft, which has an external thread, for extending into the cavity of the lower implant part, an axis of rotation, and an apposition part for contacting the upper vertebra. The two implant parts may be secured to prevent rotation about their axis of rotation. The implant also includes a ring with an internal thread, disposed between the two implant parts and interacts with the external thread of the upper implant part. Rotating the ring permits the distance between the two apposition parts to be adjusted. The ring may be axially fixed but rotatively movably with the lower implant part.

16 Claims, 3 Drawing Sheets

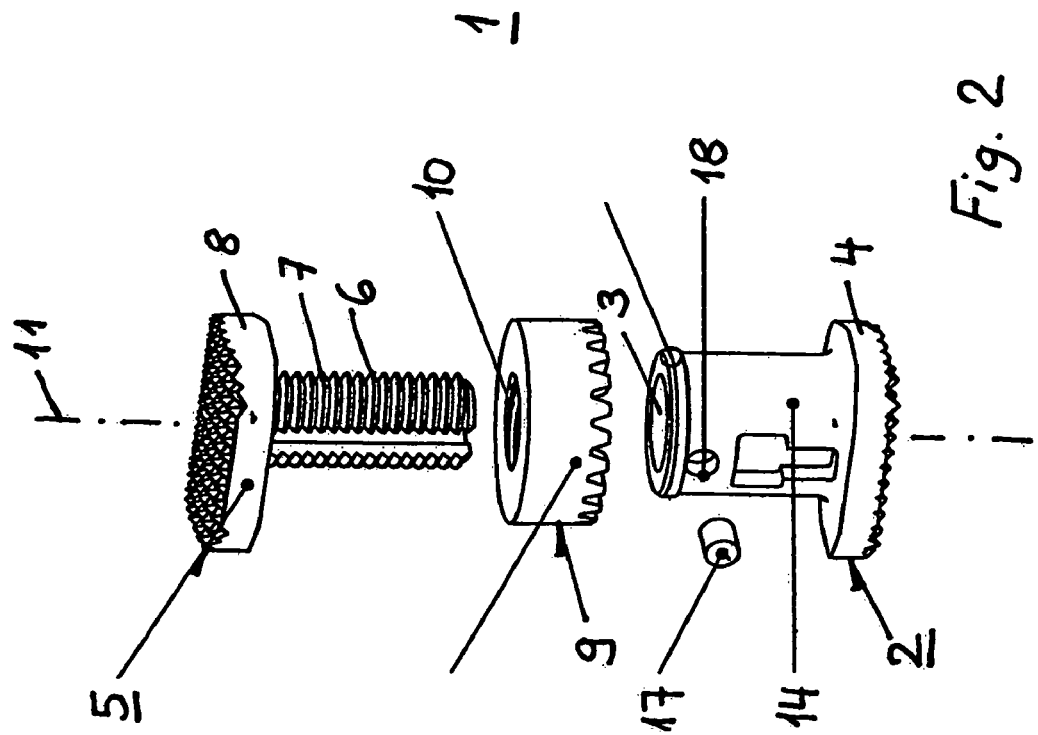
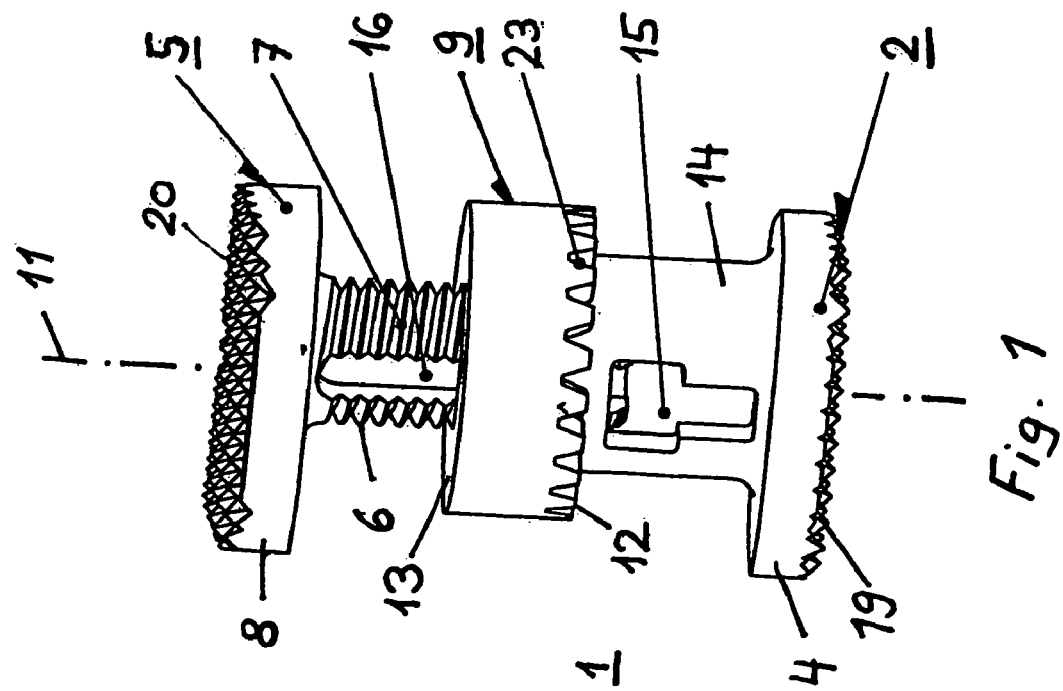

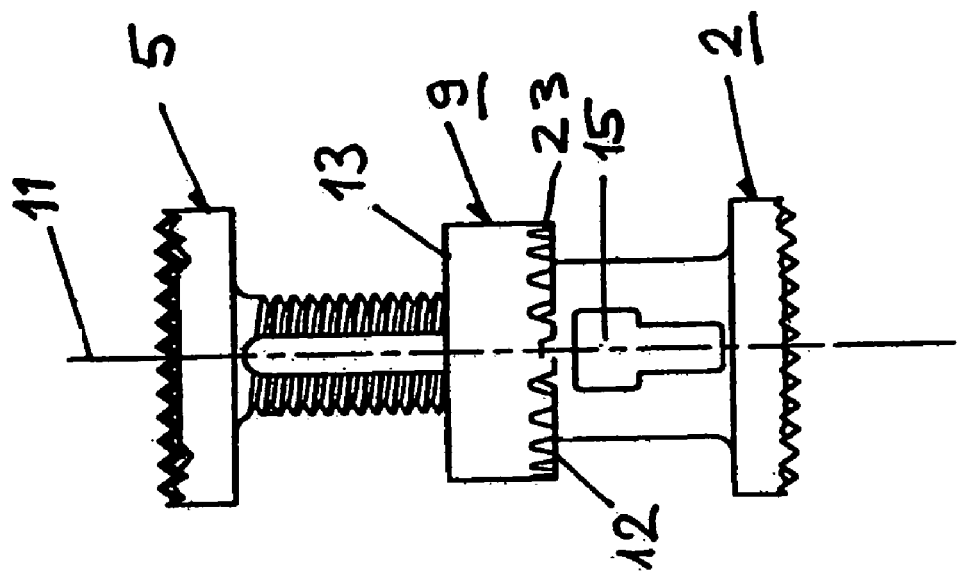
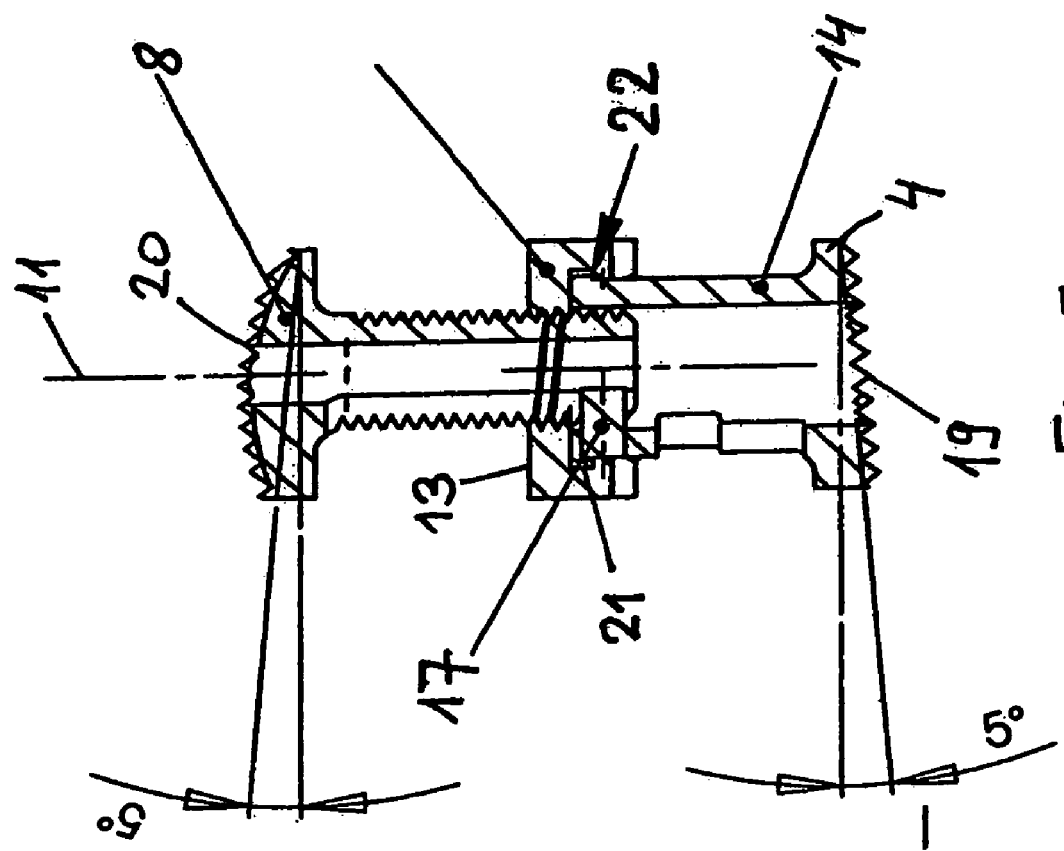

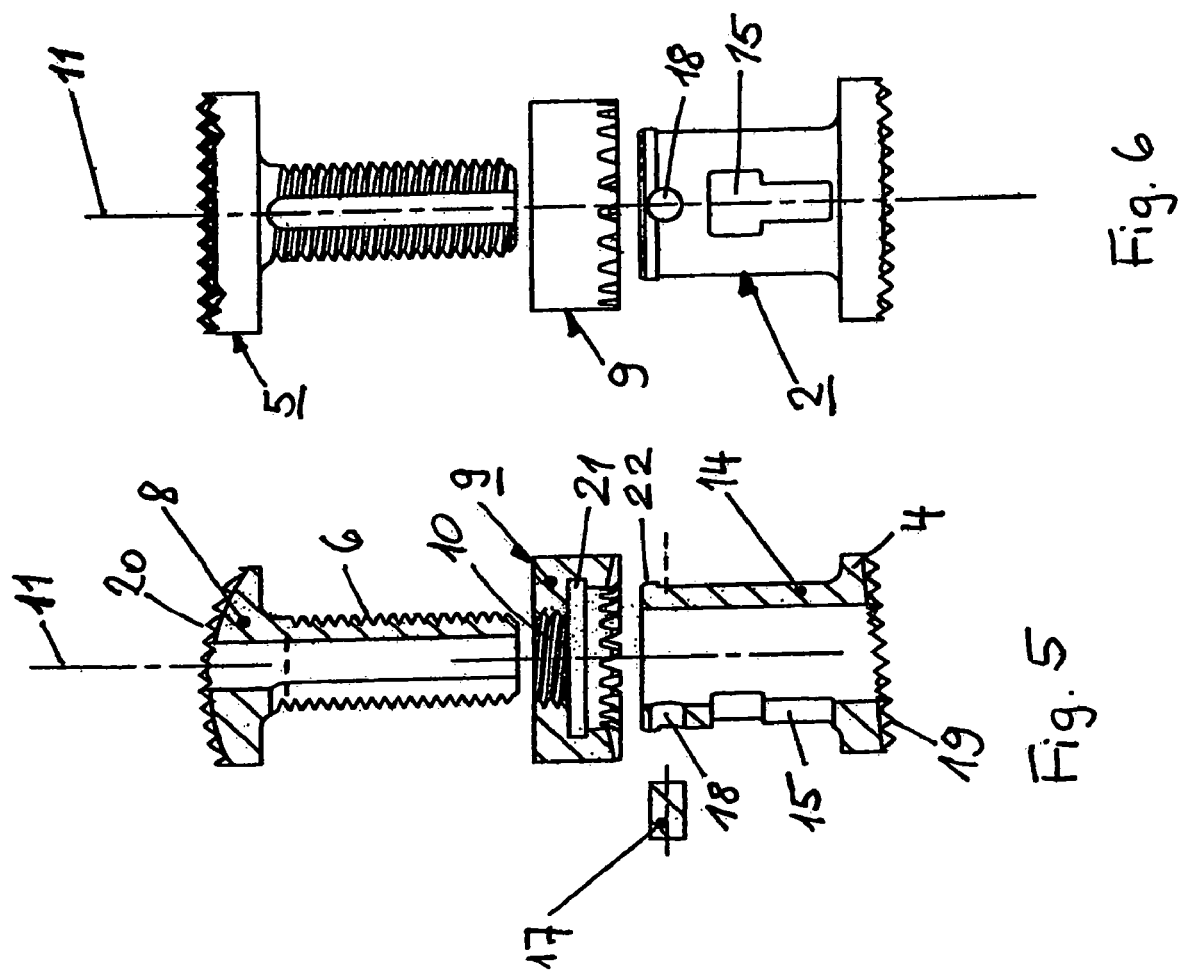

INTERVERTEBRAL IMPLANT

CROSS REFERENCE TO RELATED APPLICATION

This application is a continuation of International Patent Application No. PCT/CH2003/000273, filed Apr. 28, 2003, the entire contents of which is expressly incorporated herein by reference.

TECHNICAL FIELD

The present invention relates generally to intervertebral implants.

BACKGROUND OF THE INVENTION

It is well known in the art to use intervertebral implants. German document DE-A 196 22 827 describes a generic intervertebral implant. The DE-A 196 22 827 implant is constructed as a ring with an internal thread. A central feature of this implant is that there is a thread connection only with the upper, terminal part of the implant. The ring is freely movable axially, as well as rotatively with respect to the lower, terminal part of the implant. The lower, terminal part of the implant serves only as an axial stop for the ring. That is, as a supporting surface against which the ring can be twisted so that the upper, terminal part of the implant can be moved axially (nut/spindle driving mechanism). The two terminal implant parts accordingly are mounted loosely with respect to one another. The DE-A 196 22 827 implant also includes a radial, threaded borehole, through which a braceable clamping screw is passed in one of the two implant parts in order to secure the latter axially. A disadvantage of this intervertebral is that it is not secured before or during the surgery and can fall apart. For sterility reasons, there may be an appreciable time delay if an implant part were to fall to the floor of the operating room.

EP-A 1 219 266 (Ulrich) discloses a telescopable intervertebral prosthesis with a threaded ring which has straight bevel gear teeth, and that can be rotated from the radial direction over a bevel pinion. A disadvantage of the Ulrich device is that the threaded ring is not firmly connected axially with one of the sleeve parts. As a result, the implant is constructed less stably and, moreover, there is a need for a special instrument in order to bring about the traction of the implant. The bevel gear teeth, which are less "forgiving", is a further disadvantage of this implant. In the case of a slight, axial displacement of the bevel gear teeth, the driving instrument can no longer carry out its function and the surgeon must place the instrument once again in situ.

SUMMARY OF THE INVENTION

The present invention is to provide a remedy for the above-discussed disadvantages. It is an object of the invention to create an intervertebral implant, which, while retaining the least possible overall height, forms a compact whole. The individual parts are secured together so that they cannot fall apart and are made available to the surgeon as a preinstalled set. The structure of the implant allows for simplified handling, thereby increasing safety and reducing implantation time.

The present invention accomplishes the objective set out above with an intervertebral implant, comprising a lower implant part having a hollow cylindrical cavity with an outer casing and an axis of rotation and an apposition part intended for contacting the covering surface of the adjoining lower vertebra. The intervertebral implant also includes an upper implant part with an essentially circularly, cylindrical shaft having an external thread and an axis of rotation and an apposition part intended for contacting the covering surface of the adjoining upper vertebra, wherein the shaft extends into the cavity of the lower implant part. The implant further includes a ring with an internal thread which is disposed between the upper implant part and the lower implant part and interacts with the external thread of the upper implant part. The upper implant part and the lower implant part are secured to prevent rotation about the axis of rotation. Also, the upper implant part, the lower implant part, and the ring are disposed coaxially along the axis of rotation so that by rotating the ring on the external thread of the shaft, the distance between the two apposition parts can be infinitely variably changed. The ring is axially fixed but rotatively movably with the lower implant part, and the ring has a lower annular surface facing the lower implant part and an upper annular surface facing the upper implant part, the lower annular surface having a ring gear suitable for accommodating a corresponding pinion. The ring gear may be straight-cut.

In another embodiment, the ring is axially fixed but rotatively movably by means of a clip connection at the lower implant part. The clip connection is formed from a toroidal undercut in the ring and, corresponding therewith, an annular bead at the free and of the outer casing of the lower implant part.

In a further embodiment, the outer casing of the lower implant part has a radial depression, which is suitable for positioning and supporting a pinion with respect to the ring gear. The depression may be continuous In still a further embodiment, safeguarding against rotation of the upper implant part with respect to the lower implant part, the circularly, cylindrical shaft of the upper implant part has a guiding slot which extends parallel to the axis of rotation, and the outer casing of the lower implant part, at its inside, has an inwardly protruding guiding element which engages the guiding slot and can be introduced preferably through a radial opening in the outer casing.

In a further embodiment, the circularly, cylindrical shaft of the upper implant part has a smaller circumference than does the hollow cylindrical cavity of the lower implant part, so that the two components do not touch one another.

In still a further embodiment, the external thread of the circularly cylindrical shaft and the internal thread of the ring are constructed to be self-locking. The external thread pitch and of the internal thread pitch may range from 0.5 to 1.0 mm and preferably from 0.6 to 0.8 mm. The external thread as well as the internal thread may be constructed as right-handed threads. Still further, the external thread as well as the internal thread may be constructed as multiple threads, preferably as double-lead threads.

In another embodiment, the two apposition parts, each having an apposition surface, may be constructed as panel-shaped elements which are aligned transversely to the axis of rotation with an apposition surface intended to be in contact with the covering surface of the adjoining vertebra. The apposition surfaces are not disposed orthogonally to the axis of rotation and, preferably, enclose an angle of 83° to 85° with the axis of rotation. In a further embodiment, the two apposition surfaces may enclose an angle of 10° to 14° with one another. At least one of the two apposition surfaces, preferably that of the upper implant part, may be curved to the outside and the apposition surface of the lower implant part may be constructed essentially flat.

In yet another embodiment, an intervertebral implant includes a lower implant part having a hollow cylindrical cavity with an outer casing and an axis of rotation and an apposition part intended for contacting the covering surface of the adjoining lower vertebra, and an upper implant part with an essentially circularly, cylindrical shaft having an external thread and an axis of rotation and an apposition part intended for contacting the covering surface of the adjoining upper vertebra, wherein the shaft extends into the cavity of the lower implant part. The implant further includes a ring with an internal thread which is disposed between the upper implant part and the lower implant part and interacts with the external thread of the upper implant part. The upper implant part, the lower implant part and the ring are disposed coaxially along the axis of rotation, so that by rotating the ring on the external thread of the shaft, the distance between the two apposition parts can be infinitely variably changed, and the ring has a lower annular surface facing the lower implant part and an upper annular surface facing the upper implant part, the lower annular surface having a ring gear suitable for accommodating a corresponding pinion.

Other objectives and advantages in addition to those discussed above will become apparent to those skilled in the art during the course of the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims that follow the description for determining the scope of the invention.

BRIEF DESCRIPTION OF THE DRAWINGS

The intervertebral implant is explained in even greater detail in the following exemplary drawings. The intervertebral implant may be better understood by reference to the following drawings, wherein like references numerals represent like elements. The drawings are merely exemplary to illustrate the structure, operation and method of use of the multi-mode lighter and certain features that may be used singularly or in combination with other features and the invention should not be limited to the embodiments shown.

FIG. 1 shows a perspective view of the intervertebral implant in the assembled state, FIG. 2 shows a perspective view of the intervertebral implant in the disassembled state, FIG. 3 shows a longitudinal section through the axis of rotation of the intervertebral implant of FIG. 1, FIG. 4 shows front view of the intervertebral implant of FIG. 1, FIG. 5 shows a longitudinal section through the axis of rotation of the intervertebral implant of FIG. 1 in the disassembled state and FIG. 6 shows a front view of the intervertebral implant of FIG. 1 in the disassembled state.

DESCRIPTION OF THE PREFERRED EMBODIMENTS

The intervertebral implant 1, shown in FIGS. 1 to 6, consists of a lower implant part 2, an upper implant part 5, and a ring 9, which is disposed between the two implant parts 2, 5. The lower implant part 2 has a hollow cylindrical cavity 3 with an outer casing 14 and an axis of rotation 11, and an apposition part 4 which is intended to be in contact with the covering surface of the adjoining lower vertebra. The upper implant part 5 has an essentially circularly, cylindrical shaft 6 with an external thread 7 and an axis of rotation 11, which extends into the cavity 3 of the lower implant part 2, and an apposition part 8, which is intended to be in contact with the covering surface of the adjoining upper vertebra. The two implant parts may be secured against rotating about their axis of rotation 11.

The ring 9 may have an internal thread 10, which interacts with the external thread 7 of the upper implant part 5. The two implant parts 2, 5 and the ring 9 may be disposed coaxially along their common axis of rotation 11, so that, by rotating the ring 9 on the external thread 7 of the shaft 6, the distance between the two apposition parts 4, 8 can be changed. By means of a clip connection, the ring 9 may be connected axially fixed but rotatively movably with the lower implant part 2. As shown in FIG. 3, the clip connection may consist of a toroidal undercut 21 in the ring 9 and, corresponding thereto, an annular bead 22 at the free end of the outer casing 14 of the lower implant part 2.

The ring 9 may have a lower annular surface 12 which faces the lower implant part 2, and an upper annular surface 13 which faces the upper implant part. The lower annular surface 12 may have a straight-cut ring gear 23 which is suitable for accommodating a corresponding pinion. Compared to a taper-cut or helical-cut ring gear, a straight-cut gearing is "more forgiving".

The outer casing 14 of the lower in plant part 2 has a radially continuous depression 15 which is suitable for positioning and supporting a pinion (not shown) with respect to the ring gear 23. As a result of this configuration, after traction of the vertebra, bone chips can be introduced through the continuous depression into the cavity of the lower implant part.

As a safeguard against rotation of the upper implant part 5 with respect to the lower implant part 2, the circularly cylindrical shaft 6 of the upper implant part 5 may have a guiding slot 16, which extends parallel to the axis of rotation 11, and the outer casing 14 of the lower implant part 2, at its inside, may have an inwardly protruding guiding element 17 (FIG. 2), which engages the guiding slot 16 and can be introduced through a radial opening 18 in the outer casing 14. The external thread 7 of the circularly cylindrical shaft 6 and the internal thread 10 of the ring 9 may be constructed to be self-locking. Due to the self-locking feature of the threads, the implant 1 can be stretched to any height without the need for any additional locking devices. The pitch of the external thread 7 and of the internal thread 10 may range from 0.5 to 1.0 mm, preferably from 0.6 to 0.8 mm, and more specifically 0.7 mm. Larger pitches, for example of the order of 2 mm, displayed intraoperative disadvantages because the traction turned out to be too coarse. Smaller pitches resulted in temporally longer rotation. The external thread 7 as well as the internal thread 10 may as well be right-handed threads. This has the advantage that the instrument, which carries the pinion, can be rotated in the usual manner in the right-handed direction like a normal screwdriver, so as to stretch the implant. In another embodiment, the external thread 7 as well as the internal thread 10 are constructed as multiple threads, preferably as double-lead thread. In the case of a double-lead thread, a double lift is achieved by one revolution of the ring. Consequently, the implant is handled more rapidly and more easily, so that the time required for surgery is shortened to the benefit of the patient.

As shown in FIG. 3, the two apposition parts 4, 8 may be constructed as panel-shaped elements, disposed transversely to the axis of rotation 11, with apposition surfaces 19, 20 intended for contacting the covering surface of the adjoining vertebra. The apposition surfaces 19, 20 are not disposed orthogonally to the axis of rotation 11 and, instead, may enclose an angle of between 83° and 85° with the axis of rotation 11 so that a better adaptation to anatomical relationships results. Preferably, the two apposition surfaces 19, 20 enclose an angle of between 10° and 14° with one another, and more specifically 10°. By these means, it is possible to ensure the anatomic lordisis angle. In one embodiment of the invention, at least one of the two apposition surfaces, preferably that of the upper implant part is curved towards the outside, so that optimum adaptation to the vertebrae results. The apposition surface of the lower implant part preferably is constructed essentially flat.

The intervertebral implant may be produced from conventional implant materials. Preferably, x-ray-transmitting PEEK is used, in order to permit an evaluation of the fusion by means of x-ray beams. The intervertebral implant is particularly suitable as a vertebrae replacement in the cervical and higher thoracic region of the spinal column.

In one embodiment, the ring 9 of the intervertebral implant 1 is fastened such that it is axially fixed but rotatively movably by a clip connection at the lower part 2 of the implant 1. Accordingly, the ring 9 remains securely in position for the driving mechanism. That is, the ring 9 cannot escape axially. Preferably, the clip connection is formed from a toroidal undercut in the ring and an annular bead corresponding thereto at the free end of the outer casing of the lower implant. By these means, rotation of the ring 9 is assured in such a manner that it and the two sleeve-shaped implant parts rotate about the same center.

In the case of another embodiment, the ring 9 has a lower annular surface, which faces the lower implant part 2, and an upper annular surface, which faces the upper implant part 5. The lower annular surface may have a ring gear which is suitable for accommodating a corresponding pinion. Radially rotating the instrument carrying the pinion permits axial rotation of the ring 9. An advantage of the implant of the present embodiment, in comparison to known implants in the art for which a ring must be moved tangentially, is that less space is required for the rotating instrument. Furthermore, the procedure for inserting the implant 1 into a patient can be carried out more quickly because the instrument can be infinitely variably rotated without the need for introducing the rotating instrument time and again into new boreholes of the ring 9.

In still a further embodiment, the circular, cylindrical shaft 6 of the upper implant part has a guiding slot, which extends parallel to the axis of rotation, as a safeguard to prevent rotation of the upper implant part with respect to the lower implant part. The outer casing 14 of the lower implant part 2, at its inside, has an inwardly protruding guiding element 17, which engages the guiding slot of the upper implant part 5 and can be brought into the outer casing 14 preferably through a radial opening. By these means, mutual rotation of the two implant parts 2, 5 is prevented. Mutual rotation would adversely affect the contact between the implant and the end plates and the lordosing angles.

In another embodiment, the circular, cylindrical shaft 6 of the upper implant part 5 has a smaller circumference than does the hollow cylindrical cavity 3 of the lower implant part 2, so that the two components do not touch one another.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An intervertebral implant comprising:
a lower implant part having a hollow cylindrical cavity with an outer casing and an axis of rotation, and an apposition part intended for contacting a covering surface of an adjoining lower vertebra, the cavity in communication with a depression extending through the outer casing;
an upper implant part having an essentially circularly, cylindrical shaft having an external thread and an axis of rotation, and an apposition part intended for contacting a covering surface of an adjoining upper vertebra, wherein the shaft extends into the cavity of the lower implant part; and
a circular ring with an internal thread which is disposed between the upper implant part and the lower implant part and interacts with the external thread of the upper implant part,
wherein the upper implant part and the lower implant part are secured to prevent rotation about the axis of rotation,
wherein the upper implant part, the lower implant part and the ring are disposed coaxially along the axis of rotation, so that by rotating the ring on the external thread of the shaft, a distance between the two apposition parts can be variably changed,
wherein the ring includes a toroidal undercut and the outer casing of the lower implant part includes an annular bead, the toroidal undercut mates with the annular bead so that the ring is axially fixed but rotatively movably with the lower implant part, the toroidal undercut and the annular bead forming a continuous cylinder about the intervertebral implant; and
wherein the ring has an outer surface, an inner surface, a lower annular surface facing the lower implant part and an upper annular surface facing the upper implant part, the ring including a straight-cut ring gear suitable for accommodating a corresponding pinion, the straight-cut ring gear extending from the outer surface to the inner surface, and from the lower annular surface thereof.

2. An intervertebral implant according to claim 1, wherein the depression is comprised of a radially continuous depression, which is suitable for positioning and supporting a pinion with respect to the ring gear.

3. An intervertebral implant according to claim 1, wherein the circularly, cylindrical shaft of the upper implant part includes a guiding slot which extends parallel to the axis of rotation, and the outer casing of the lower implant part includes an inwardly protruding guiding element which engages the guiding slot to prevent rotation of the upper implant part with respect to the lower implant part, the guiding element being insertable via a radial opening formed in the outer casing.

4. An intervertebral implant according to claim 1, wherein the circularly, cylindrical shaft of the upper implant part has a smaller circumference than does the hollow cylindrical cavity of the lower implant part, so that the two components do not touch one another.

5. An intervertebral implant according to claim 1, wherein the external thread of the circularly cylindrical shaft and the internal thread of the ring are constructed to be self-locking.

6. An intervertebral implant according to claim 5, wherein the external thread pitch and the internal thread pitch ranges from 0.5 to 1.0 mm.

7. An intervertebral implant according to claim 1, wherein the external thread as well as the internal thread are constructed as right-handed threads.

8. An intervertebral implant according to claim 1, wherein the external and internal threads are constructed as double-lead threads.

9. An intervertebral implant according to claim 1, wherein the two apposition parts, each having an apposition surface, are constructed as panel-shaped elements which are aligned transversely to the axis of rotation with an apposition surface intended to be in contact with the covering surface of the adjoining vertebra.

10. An intervertebral implant according to claim 9, wherein the apposition surfaces form an angle between 83 degrees and 85 degrees with the axis of rotation.

11. An intervertebral implant according to claim 10, wherein the two apposition surfaces enclose an angle of 10 degrees to 14 degrees with one another.

12. An intervertebral implant according to claim 9, wherein at least one of the two apposition surfaces is curved to the outside.

13. An intervertebral implant according to claim 9, wherein the apposition surface of the lower implant part is constructed essentially flat.

14. An intervertebral implant comprising:
   a lower implant part having a hollow cylindrical cavity with an outer casing and an axis of rotation, and an apposition part intended for contacting a covering surface of an adjoining lower vertebra, the outer casing having a depression extending therethrough and being in communication with the cavity;
   an upper implant part with an essentially circularly, cylindrical shaft having an external thread and an axis of rotation, and an apposition part intended for contacting a covering surface of an adjoining upper vertebra, wherein the shaft extends into the cavity of the lower implant part; and
   a circular ring with an internal thread which is disposed between the upper implant part and the lower implant part and interacts with the external thread of the upper implant part,
   wherein the ring includes a toroidal undercut and the outer casing of the lower implant part includes an annular bead, the toroidal undercut mates with the annular bead so that the ring is axially fixed but rotatively movably with the lower implant part, the toroidal undercut and the annular bead forming a continuous cylinder about the intervertebral implant;
   wherein the upper implant part, the lower implant part and the ring are disposed coaxially along the axis of rotation, so that by rotating the ring on the external thread of the shaft, a distance between the two apposition parts can be variably changed,
   wherein the ring has an outer surface, an inner surface, a lower annular surface facing the lower implant part and an upper annular surface facing the upper implant part, the ring including a straight-cut ring gear suitable for accommodating a corresponding pinion, the straight-cut ring gear extending from the outer surface to the inner surface, and from the lower annular surface thereof, the ring gear being located on a plane generally perpendicular to the axis of rotation; and
   wherein the upper implant part, the lower implant part and the ring are made from an X-ray-transmitting material.

15. The intervertebral implant of claim 14 wherein the X-ray transmitting material is a PEEK material.

16. An intervertebral implant comprising:
   a lower implant part having a hollow cavity and an axis of rotation, and an apposition part intended for contacting an adjoining lower vertebra, the hollow cavity in communication with a depression in the lower implant part;
   an upper implant part having a shaft having an external thread and an axis of rotation, and an apposition part intended for contacting an upper vertebra, wherein the shaft extends into the cavity of the lower implant part; and
   a circular ring disposed between the upper implant part and the lower implant part, the ring having an internal thread for engaging the external thread of the upper implant part;
   wherein the upper implant part and the lower implant part are secured to prevent rotation about the axis of rotation;
   wherein rotating the ring about the shaft causes a change in distance between the two apposition parts; and
   wherein the ring is axially fixed but rotatively movably with respect to the lower implant part, the ring and lower implant part being coupled together by a continuous surface that extends circumferentially about the axis of rotation; and
   wherein the ring has an outer surface, an inner surface, a lower annular surface facing the lower implant part and an upper annular surface facing the upper implant part, the ring including a straight-cut ring gear suitable for accommodating a corresponding pinion, the straight-cut ring gear extending from the outer surface to the inner surface, and from the lower annular surface thereof, the ring gear facing directly toward the apposition part of the lower implant part.

* * * * *